United States Patent
Schneider (10) Patent No.: US 11,410,762 B2
(45) Date of Patent: *Aug. 9, 2022

(54) MEDICATION REQUISITION FULFILLMENT SYSTEM AND METHOD

(71) Applicant: BAXTER CORPORATION ENGLEWOOD, Englewood, CO (US)

(72) Inventor: Dennis I. Schneider, Nashua, NH (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 108 days.

This patent is subject to a terminal disclaimer.

(21) Appl. No.: 16/739,837

(22) Filed: Jan. 10, 2020

(65) Prior Publication Data

US 2020/0152306 A1 May 14, 2020

Related U.S. Application Data

(63) Continuation of application No. 14/424,959, filed as application No. PCT/US2013/031707 on Mar. 14, 2013, now Pat. No. 10,552,577.

(Continued)

(51) Int. Cl.
*G16H 20/10* (2018.01)
*G16H 40/20* (2018.01)
*G16H 20/17* (2018.01)

(52) U.S. Cl.
CPC ............ *G16H 20/10* (2018.01); *G16H 20/17* (2018.01); *G16H 40/20* (2018.01)

(58) Field of Classification Search
CPC ........ G16H 10/60; G16H 40/20; G16H 10/20; G16H 10/40; G16H 15/00; G16H 20/17; G16H 20/70; G16H 40/67; G16H 70/20

(Continued)

(56) References Cited

U.S. PATENT DOCUMENTS

2005/0177392 A1 8/2005 Domashnev
2007/0088594 A1 4/2007 Goodall et al.
(Continued)

FOREIGN PATENT DOCUMENTS

JP 2003022322 A 1/2003
JP 2004078970 A 3/2004
(Continued)

OTHER PUBLICATIONS

Guimarães, Cristina Machado; Outsourcing in Healthcare Through Process Modularization—A Lean Perspective; International Journal of Engineering Business Management 4 Sage Publications Ltd. (2012) : (Year: 2012).*

(Continued)

*Primary Examiner* — Hiep V Nguyen
(74) *Attorney, Agent, or Firm* — K&L Gates LLP (57) ABSTRACT

A system and associated method are provided for fulfillment of medication requisitions corresponding to contained medication units. Requisition fulfillment logic may be included to provide decision data to a patient care provider for use in selecting one of a plurality of different fulfillment sites to fill a given medication requisition. A requisition router may route the medication requisition to a selected one of the plurality of fulfillment sites. The fulfillment sites may provide medication requisition metadata (e.g., data relating to the preparation and handling of medication units) to a medication requisition database in corresponding relation to the corresponding medication requisitions fulfilled by the fulfillment sites. The medication requisition metadata may be stored in the medication requisition database and accessed to facilitate enhanced management functionalities in relation to medication units dispensed by patient care providers.

20 Claims, 2 Drawing Sheets

Related U.S. Application Data (60) Provisional application No. 61/695,831, filed on Aug. 31, 2012.

(58) Field of Classification Search
USPC .......................................................... 705/2
See application file for complete search history.

(56) References Cited

U.S. PATENT DOCUMENTS

| | | | |
|---|---|---|---|
| 2007/0088596 | A1 | 4/2007 | Berkelhamer et al. |
| 2008/0300794 | A1* | 12/2008 | Greyshock ............... G06K 9/32 702/19 |
| 2008/0306761 | A1 | 12/2008 | George et al. |
| 2009/0198520 | A1 | 8/2009 | Piovanetti-Perez |
| 2010/0094653 | A1 | 4/2010 | Tribble et al. |
| 2010/0125461 | A1 | 5/2010 | Heald et al. |
| 2011/0267465 | A1 | 11/2011 | Alexander et al. |
| 2013/0173277 | A1* | 7/2013 | Eller ...................... G16H 40/67 705/2 |

FOREIGN PATENT DOCUMENTS

| | | |
|---|---|---|
| JP | 2004232557 A | 8/2004 |
| JP | 2005269257 A | 9/2005 |
| WO | WO-02097571 A2 * 12/2002 ........... G06F 19/322 |
| WO | 2009137863 A1 11/2009 |

OTHER PUBLICATIONS

Korean Office Action and English translation for related Korean Application No. 10-2019-7028895; dated Mar. 23, 2020; (6 pages).
Korean Office Action for related Korean Application No. 10-2019-7028895; dated Jan. 13, 2020; (8 pages).
Extended European Search Report for related European Application No. 19214907.8; dated Mar. 31, 2020; (10 pages).
Australian Examination Report for related Australian Application No. 2019203303; dated Nov. 4, 2020; (6 pages).
Korean Office Action for related Korean Application No. 10-2020-7019178; dated Mar. 16, 2021; (3 pages).
Korean Office Action for related Korean Application No. 10-2020-7019178; dated Sep. 29, 2020; (16 pages).
Australian Examination Report for related Australian Application No. 2019203303; dated Jul. 29, 2020; (5 pages).
Korean Office Action for related Korean Application No. 10-2021-7016693; dated Sep. 27, 2021; (6 pages).
Canadian Office Action for related Canadian Application No. 2,883,273; dated Jul. 7, 2021; (4 pages).
Australian Examination Report No. 2 for AU Patent Application No. 2021201530, dated Mar. 31, 2022.

* cited by examiner

FIG. 1

FIG. 2

US 11,410,762 B2

MEDICATION REQUISITION FULFILLMENT SYSTEM AND METHOD

PRIORITY CLAIM

This application is a continuation of U.S. patent application Ser. No. 14/424,959 filed Feb. 27, 2015, entitled "MEDICATION REQUISITION FULFILLMENT SYSTEM AND METHOD," which is a national stage entry of PCT Application No. PCT/US2013/031707 filed Mar. 14, 2013, entitled "MEDICATION REQUISITION FULFILLMENT SYSTEM AND METHOD," which claims priority to U.S. Provisional Patent Application No. 61/695,831 filed Aug. 31, 2012, entitled "MEDICATION REQUISITION FULFILLMENT SYSTEM AND METHOD," each of which is incorporated herein by reference in its entirety.

FIELD OF THE INVENTION

The present invention relates to a system and associated method for fulfillment of a medication requisition to be dispensed by a patient care provider for administration to a patient.

BACKGROUND OF THE INVENTION

Patient care providers routinely dispense medication units for administration to patients in the course of providing health care services. In this regard, the dispensing and administration of medication units may require authorization by a governing regulatory body. The medication units may be prepared and/or otherwise dispensed by a pharmacy located at or otherwise affiliated with a given patient care provider or by third-party source(s). For example, many hospitals have an onsite pharmacy from which medication units may be dispensed after preparation at the pharmacy.

A number of factors may present logistical challenges to a patient care provider in fulfilling medication requisitions. For example, each medication unit to be dispensed by a given patient care provider may have a different associated fulfillment timing requirement to ensure timely dispensing and administration of the medication unit to the corresponding patient. Additionally, the scope of inventory needed for a pharmacy to accommodate a wide range of potential medication units may be difficult to maintain, particularly in relation to medication unit components having a limited shelf-life, demanding handling/storage requirements and/or otherwise experiencing supply shortages. Also, the preparation of certain types of medication units necessitates specialized equipment, facilities and skills that may not be commonly available, thereby limiting sourcing options. Further, cost efficiencies may be unavailable to many patient care providers.

In addition to the foregoing, an emphasis on detailed record-keeping for medication units continues to grow in the healthcare field. Such record-keeping may entail the obtainment and storage of various data pertaining to the preparation and handling of medication units. In this regard, the administrative burden associated with such record-keeping continues to increase.

Currently, existing approaches for obtaining medication units largely entail source selection processes in which limited and/or static data is utilized to make a selection and/or in which sourcing selection options are otherwise limited.

SUMMARY OF THE INVENTION

The present disclosure generally relates to an improved system and associated method for fulfillment of a medication requisition to be dispensed by a patient care provider for administration to a patient.

In one aspect, an improved system comprises a requisition generator and a requisition fulfillment logic provided for use by a patient care provider. The requisition generator may be employed to generate a medication requisition for at least one contained unit of a medication to be dispensed by the patient care provider and administered to a patient. The requisition fulfillment logic may be executed by a computer-based tool to process a medication requisition and provide decision data for use in selecting one of a plurality of different fulfillment sites to fulfill the medication requisition. The decision data may be based, at least in part, on one of medication requisition fulfillment cost data and/or medication requisition fulfillment timing data corresponding with each of the plurality of fulfillment sites. The system may further include a requisition router to route a given medication requisition to a selected fulfillment site that is selected from the plurality of fulfillment sites for preparation of the medication requisition.

Accordingly, the system relieves a user of the patient care provider from, and/or assists user of the patient care provider in, the mental task of e.g. keeping track of inventory/availability of medication units with relation to fulfillment sites. Even more, the user may obtain the medication unit that best suits the patient care provider's needs from the appropriate fulfillment site. Moreover, the system implements improved man machine interaction, since the requisition router may route the medication requisition to the selected fulfillment site without the necessity of an interaction with the user of the patient care provider. In the context of this application, the term user of a patient care provider may relate to a human person, such as and not limited to an employee or an owner of a patient care provider.

As may be appreciated, the provision of a system having requisition fulfillment logic to provide decision data may facilitate the realization of enhanced cost efficiencies and/or timely medication requisition fulfillment by a patient care provider. For example, the decision data may be provided to assist the patient care provider in assessing trade-offs between utilizing different fulfillment sites in relation to a given medication requisition.

In contemplated embodiments, at least one or more than one of the plurality of fulfillment sites may be located remotely relative to the patient care provider. Further, at least another one of the plurality of fulfillment sites may be located at a patient care provider site corresponding with the patient care provider. For example, the patient care provider may have a pharmacy onsite or otherwise affiliated therewith. Hence, the system may, in an automated manner, allow a user of the patient care provider to select the most appropriate of a number of fulfillment sites without the necessity of accessing the individual fulfillment site. Moreover, the user of the patient care provider can reduce processing power at the patient care provider's site, by accessing and/or using processing power of one or more fulfillment sites.

In contemplated implementations, the patient care provider may comprise an entity that is authorized by a governing regulatory body to dispense medication requisitions. Further, the patient care provider may be an entity that is authorized by a governing regulatory body to prepare medication requisitions.

By way of primary example, the patient care provider may comprise one of the following:
- an acute care site;
- a hospital;
- a home infusion pharmacy;
- a physician office; or,
- a free-standing infusion clinic.

In relation to the contemplated system, a contained medication unit corresponding with a given medication requisition may be obtained by a patient care provider from a selected fulfillment site for dispensing by the patient care provider for administration to a patient. In this regard, the contained medication unit may comprise one of the following:
- a patient specific unit comprising a medication unit designated for administration to a specific patient;
- a non-patient specific unit comprising a medication unit to be subsequently designated for administration to a specific patient; or,
- a medication component source unit to be used in the preparation of a patient specific unit or a non-patient specific unit (e.g., that will be designated for administration to a specific patient after preparation).

In some instances, the contained medication unit may comprise a nutritional supplement or a component of a nutritional supplement that requires administration by the patient care provider. By way of example, a contained medication unit may comprise a parenteral nutrition supplement (e.g., a total parenteral nutrition or total nutrient admixture).

In some implementations, a contained medication unit may be received by the patient care provider from a remote fulfillment site, wherein the contained medication unit may be associated with a kit comprising a plurality of contained medication units (e.g., a container used for handling the corresponding plurality of medication units). The association may be obtained or defined in a database and/or a table of a database that identifies for each contained medication unit a corresponding kit. Accordingly, for each contained medication unit and for each kit there may be a direct relation between exactly one specific contained medication unit and one specific kit. In this regard, the different medication requisitions corresponding with the plurality of contained medication units comprising the kit may be associated with a corresponding kit identifier, thereby facilitating various record-keeping functionalities, e.g., the obtainment and maintenance of certain medication requisition metadata referenced hereinbelow. For example, a kit identifier (e.g., a machine-readable marking on a container used for handling the corresponding plurality of medication units) may be utilized to facilitate data collection in relation to the location, handling, etc., of the associated medication units. Accordingly, the system allows in a simple and efficient manner to provide a specific contained medication unit with a number (i.e., a kit of) contained medication units, and maintain records relating thereto, without needing to separately obtain/record information for each individual/specific medication unit (e.g., in relation to location, handling, etc.). In particular, in view of the complexity of organizing a chain of products, the system provides in a simple and automated manner obtaining a specific medication unit while providing a kit of medication units. The system may particularly comprise a computing environment implementing or being part of the requisition generator and/or the requisition fulfillment logic and/or the requisition router.

As noted, the system may comprise requisition fulfillment logic to provide decision data based in part on at least one of medication requisition fulfillment cost data and/or medication requisition fulfillment timing data corresponding with each of a plurality of fulfillment sites. Such data may be stored and otherwise maintained in a medication requisition database.

The medication requisition fulfillment timing data may comprise at least one of the following:
- medication requisition fulfillment lead time data;
- medication requisition availability data;
- medication requisition delivery schedule data;
- medication requisition efficacy timing data; and/or,
- medication unit component efficacy timing data.

The medication requisition fulfillment cost data may comprise data indicative of a cost for fulfillment of a given medication requisition by a given fulfillment site.

In contemplated system embodiments, each of the plurality of fulfillment sites may provide all or at least a portion of the medication requisition fulfillment cost data and/or medication requisition fulfillment timing data corresponding with the given fulfillment site. More particularly, such data (simply referred to as medication requisition data) may be provided by the fulfillment sites to the medication requisition database. For example, the data may be provided on a periodic, request/response, or other basis. By way of further example, the data may be provided in relation to predetermined types or otherwise specified medication units.

In some embodiments the requisition fulfillment logic may comprise one or more algorithms (e.g., stored in a computer-readable medium) for processing the medication requisition (e.g., by a computer) in relation to medication requisition fulfillment cost data and/or medication requisition fulfillment timing data stored at the medication requisition database. In one approach, an algorithm may provide for the selective establishment of weighting parameters associated with each of medication requisition fulfillment cost data and/or medication requisition fulfillment timing data (e.g., via software program instructions/user input).

In some applications, the requisition fulfillment logic may be provided to be customizable by a given patient care provider. By way of example, a given patient care provider may set algorithm weighting parameters and/or may define additional logic parameters.

In certain implementations, the requisition fulfillment logic may be operable to automatically select a fulfillment site to fulfill a given medication requisition based on the generated decision data. As may be appreciated, such automated selection functionality may be established in relation to predetermined types of medication requisitions. Further, in some embodiments, the requisition router may be operable to automatically route medication requisitions to an automatically selected fulfillment site. Accordingly, without the need of human interaction, the system may allow for efficient drug medication requisition fulfillment. In particular, the efficiency may be improved by the system becoming more failsafe as the router is not prone to errors a human may make.

In some arrangements, the selected fulfillment site may be adapted to selectively, automatically and/or semi-automatically reject a given medication requisition routed to it (e.g., in the event of unforeseen or other circumstances). In turn, a requisition rejection may be communicated by the fulfillment site (e.g., in a selective, automatic and/or semi-automatic manner) to the fulfillment logic and medication requisition database, wherein the requisition fulfillment logic is further utilized to provide decision data for use selecting a different fulfillment site. Correspondingly, the medication requisition database may be updated in relation to the medication requisition.

In contemplated embodiments, the fulfillment site selected to fulfill a given medication requisition may be adapted to provide medication requisition metadata to a medication requisition database in relation to fulfillment of the medication requisition. In this regard, the selected fulfillment site may follow predetermined procedures and/or utilize data collection tools to obtain and provide medication requisition metadata in relation to the preparation, handling, etc., of a medication unit corresponding with a given medication requisition, and to provide medication requisition metadata to the medication requisition database. In turn, the system may be provided so that the patient care provider corresponding with a given medication requisition may access at least a portion of the corresponding medication requisition metadata from the medication requisition database.

The medication requisition metadata may comprise one or more of the following types of data:
  medication source data indicative of at least one of:
    a manufacturer of a component of the contained medication unit corresponding to the medication requisition,
    a lot number of a component of the contained medication unit corresponding to the medication requisition,
    an expiration date of a component of the contained medication unit corresponding to the medication requisition,
    a serial number of a component of the contained medication unit corresponding to the medication requisition, or
    a drug code indicative of the identity of a component of the contained medication unit corresponding to the medication requisition;
  chain of custody data indicative of at least one of:
    a listing of entities in possession of a component of the contained medication unit corresponding to the medication requisition or the contained medication unit corresponding to the medication requisition,
    a listing of users that have taken an action with respect to the contained medication unit corresponding to the medication requisition, wherein the listing of users is correlated to specific actions taken by each user, or
    tracking information corresponding to physical movement of a component of the contained medication unit corresponding to the medication requisition or the contained medication unit corresponding to the medication requisition;
  fulfillment data indicative of at least one of:
    image data corresponding with a component of the contained medication unit corresponding to the medication requisition or the contained medication unit corresponding to the medication requisition,
    scanned data obtained from a component of the contained medication unit corresponding to the medication requisition,
    analytic data regarding a component of the contained medication unit corresponding to the medication requisition or the contained medication unit corresponding to the medication requisition,
    pharmacist review data corresponding with at least one pharmacist review of a component of the contained medication unit corresponding to the medication requisition or the contained medication unit corresponding to the medication requisition,
    compliance data corresponding with best practices associated with a component of the contained medication unit corresponding to the medication requisition or the contained medication unit corresponding to the medication requisition,
    sterility assessment data corresponding to a component of the contained medication unit corresponding to the medication requisition or the contained medication unit corresponding to the medication requisition,
    a listing of actions corresponding to a component of the contained medication unit corresponding to the medication requisition or the contained medication unit corresponding to the medication requisition,
    time stamp data corresponding to actions corresponding to a component of the contained medication unit corresponding to the medication requisition or the contained medication unit corresponding to the medication requisition, or
    a listing of life cycle events taken with respect a component of the contained medication unit corresponding to the medication requisition or the contained medication unit corresponding to the medication requisition; or
  environmental data indicative of at least one of:
    a temperature to which a component of the contained medication unit corresponding to the medication requisition or the contained medication unit corresponding to the medication requisition has been exposed,
    a temperature to which and corresponding time period for which a component of the contained medication unit corresponding to the medication requisition or the contained medication unit corresponding to the medication requisition has been exposed,
    whether a component of the contained medication unit corresponding to the medication requisition or the contained medication unit corresponding to the medication requisition is refrigerated,
    whether a component of the contained medication unit corresponding to the medication requisition or the contained medication unit corresponding to the medication requisition is frozen,
    a temperature profile experienced by a component of the contained medication unit corresponding to the medication requisition or the contained medication unit corresponding to the medication requisition, or
    accelerometer data corresponding to forces experienced by a component of the contained medication unit corresponding to the medication requisition or the contained medication unit corresponding to the medication requisition.

As may be appreciated, the obtainment and accessibility of medication requisition metadata may enhance the management functionality of the medication unit fulfillment system. The medication requisition metadata, in particular used and/or stored by a computer, relieves the user of the patient care provider from, and/or assists the user of the patient care provider in, the (mental) task of keeping track of and/or organizing the above mentioned data. In particular, without the (computer aided) system according to this application, the above mentioned data management and data processing would not be possible.

In various implementations, the contemplated system may include a distributed medication requisition management system that includes a distributed medication requisition management client at each of the plurality of fulfillment sites and in operative communication with the requisition router so as to receive medication requisitions from the requisition router. In turn, the system may further include a medication requisition management network that includes the distributed medication requisition management clients, the medication requisition database, and the requisition router. In such implementations, the system may be maintained so that at least portions of the corresponding medication requisition metadata are located at separate physical locations.

In another aspect, a distributed medication requisition management system may comprise a requisition generator to generate a medication requisition for at least one contained unit of a medication for dispensing by a patient care provider, and a medication requisition database operable to store the medication requisition. The system may further include a plurality of medication requisition management clients resident in a plurality of fulfillment sites capable of fulfilling a medication requisition. A medication requisition management network may be provided in operative communication with each of the plurality of medication requisition management clients, the medication requisition database, and the requisition generator, wherein the medication requisition management network is operable to provide the medication requisition to the medication requisition management client of a selected fulfillment site of the plurality of fulfillment sites. The system may be provided so that the patient care provider obtains a contained medication unit corresponding with the medication requisition from the selected fulfillment site for dispensing and administration to a corresponding patient, and wherein the selected fulfillment site provides medication requisition metadata to the medication requisition management network for storage in the medication requisition database in corresponding relation to the medication requisition.

As may be appreciated, various ones and combinations of the functionalities noted hereinabove may be utilized in the distributed medication requisition management system.

In a further aspect, a method for fulfillment of a medication requisition to be dispensed by a patient care provider, for administration to a patient is provided. In some embodiments, the method may include generating a medication requisition by use of a requisition generator by a patient care provider, wherein the medication requisition is for at least one contained unit of a medication for administration to a patient. The method may further comprise processing the medication requisition, by use of requisition fulfillment logic by a patient care provider and executed by a computer-based tool, wherein the processing provides decision data for use in selecting one of a plurality of fulfillment sites to fulfill the medication requisition. In this regard, decision data may be based at least in part on one of medication requisition fulfillment cost data or medication requisition fulfillment timing data corresponding to each of the plurality of fulfillment sites. Further, the method may include routing of the medication requisition by a requisition router to a selected fulfillment site selected from the plurality of fulfillment sites for preparation of the medication requisition.

In some embodiments, the method may further include selecting automatically, by operation of the requisition fulfillment logic, the selected fulfillment site at least partially based on the decision data. Additionally, or alternatively, the method may further comprise routing automatically, by operation of the router, the medication requisition to the selected fulfillment site for fulfillment of the medication requisition. In various method embodiments, the method may employ a system comprising any of the system features described herein.

According to yet another aspect, a computer program product is provided that can be stored on a computer readable medium and/or can be implemented as computer processable data stream, wherein the computer program product comprises computer processable instructions, which instructions when read in the memory of a computer and executed by the computer cause the computer to carry out the method(s) as described in general above, and in more specific examples below.

Numerous additional features and advantages of the present invention will become apparent to those skilled in the art upon consideration of the embodiment descriptions provided hereinbelow.

DETAILED DESCRIPTION

Figure 1:
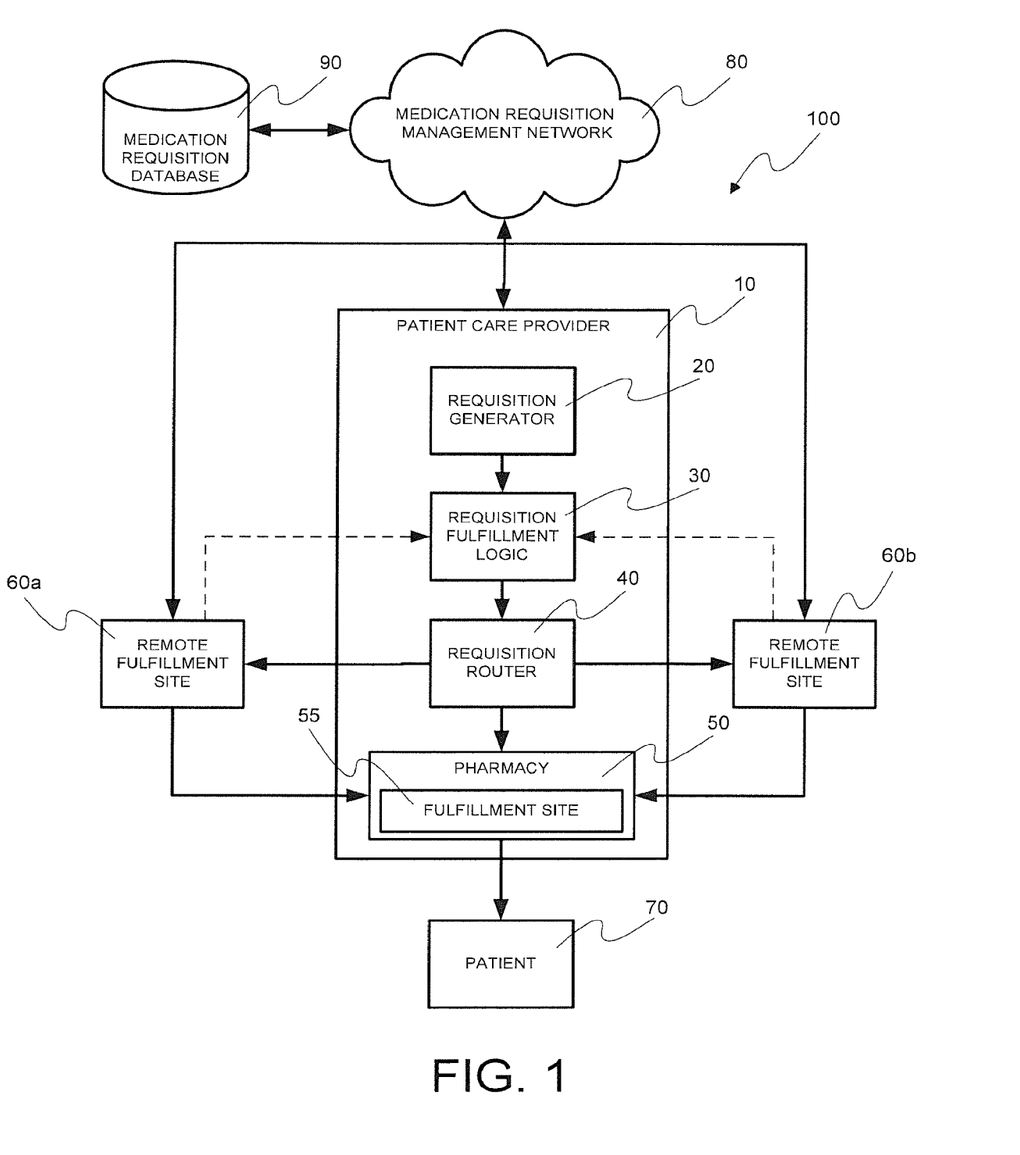
FIG. 1 illustrates an embodiment of a system for fulfillment of medication requisitions.

FIG. 1 illustrates an embodiment of a system 100 for fulfillment of a medication requisition. The medication requisition may correspond to at least one contained unit of a medication. The contained unit may comprise, for instance, one of the following:

a syringe;

a vial;

a bag; or, another medication container used in the administration of a medication to a patient or used in the course of preparation of a medication for administration to a patient.

The system 100 may include a number of components that may be used to generate a medication requisition, to prepare decision data for use in the selection of a fulfillment site for fulfillment of the medication requisition, and to route a given medication requisition to a selected fulfillment site. In this regard, the components of the system 100 may include a requisition generator 20, requisition fulfillment logic 30, and a requisition router 40, respectively. By way of example, the requisition generator 20, requisition fulfillment logic 30, and a requisition router 40 may be located at a patient care provider 10.

The requisition generator 20 may generate a medication requisition corresponding to a medication unit that is to be used or dispensed by the patient care provider 10 for administration to a patient 70. The requisition generator 20 may be operable to generate the medication requisition in an automated or partially automated manner based on an order comprising a data stream. By way of example, the order may correspond with a medication prescribed by a physician.

In one approach, the requisition generator 20 may be operable to parse or otherwise derive data from a data stream to generate the medication requisition. Additionally or alternatively, the requisition generator 20 may generate a medication requisition based on data that is received directly from a user (e.g., by way of data entry via a user interface).

The requisition generator 20 may be operable to provide the medication requisition for processing by requisition fulfillment logic 30. Requisition fulfillment logic 30 may comprise a computer-based tool (e.g., including hardware and/or software) for providing decision data for use in selecting one of a plurality of fulfillment sites to fulfill a given medication requisition. The computer-based tool may comprise a memory operable to store non-transitory machine-readable instructions that may be executed by a processor. Requisition fulfillment logic 30 may further include or access a database that may be used by the requisition fulfillment logic 30 to produce the decision data.

The data utilized by requisition fulfillment logic 30 to provide the decision data may at least include medication requisition preparation cost data and/or medication requisition preparation timing data that corresponds to a plurality of potential fulfillment sites that have the ability to fulfill the medication requisition. For example, as shown in FIG. 1, remote fulfillment site 60a, remote fulfillment site 60b, or fulfillment site 55 may all be potential fulfillment sites for fulfillment of medication requisitions.

In this regard, the requisition fulfillment logic 30 may provide the decision data to a user (e.g., provided to a user at the patient care provider 10 via a user interface device). The user may then select one of the plurality of fulfillment sites for fulfillment of the medication requisition (e.g., via input at a user interface). In an embodiment, requisition fulfillment logic 30 may automatically select a fulfillment site at least partially based on the decision data for a given medication requisition. Optionally, a determination as to whether a fulfillment site is selected by a user or automatically selected may at least partially depend upon an identifiable characteristic of a given medication requisition (e.g., dependent upon medication type, medication amount, timing requirements, or other data associated with the medication requisition). In this regard, potential time and cost savings may be realized.

As noted, a requisition router 40 may be provided to route the medication requisition to the selected fulfillment site for fulfillment of the medication requisition. As schematically presented in FIG. 1, at least one onsite fulfillment site (e.g., fulfillment site 55) and/or at least one offsite fulfillment site (e.g., fulfillment sites 60a, 60b) may be available for selection to fulfill a given medication requisition.

Regardless of the relative location of the selected fulfillment site, the requisition router 40 may be operable to communicate the medication requisition to the selected fulfillment site. The requisition router 40 may receive the identity of the selected fulfillment site from a user (e.g., a user at the patient care provider 10) or may automatically route the medication requisition order to the selected fulfillment site based on the automatic selection of a fulfillment site by the requisition fulfillment logic 30.

One or more of the fulfillment sites 60a and 60b may be adapted to selectively, automatically and/or semi-automatically reject a given medication requisition routed to it (e.g., in the event of unforeseen circumstances). In turn, a requisition rejection may be communicated by the fulfillment site 60a or 60b (e.g., in a selective, automatic and/or semi-automatic manner) to requisition fulfillment logic 30 and medication requisition database 90, wherein the requisition fulfillment logic 30 is further utilized to provide decision data for use selecting a different fulfillment site. Correspondingly, the medication requisition database 90 may be updated in relation to the medication requisition.

As stated above, the fulfillment sites may include one or more remote fulfillment sites 60a and 60b located remotely relative to the patient care provider 10. Furthermore, the patient care provider 10 may include a patient care provider site that may include a pharmacy 50. In turn, the pharmacy 50 may include a fulfillment site 55 located in the pharmacy 50. It may also be appreciated that the patient care provider 10 may be affiliated with a pharmacy 50 that is located offsite relative to the patient care provider site. In any regard, each of the fulfillment sites 55, 60a, and 60b may be capable of fulfilling a medication requisition and providing the medication unit corresponding to the medication requisition to the pharmacy 50. In turn, the pharmacy 50 may be operable to dispense the medication unit for administration to the patient 70.

Additionally, as depicted in FIG. 1, a medication requisition management network 80 may be in operative communication with remote fulfillment sites 60a and 60b, as well as the patient care provider 10. The medication requisition management network 80 may also be in operative communication with a medication requisition database 90. The medication requisition database 90 may be operable to store one or more sets, or portions, of data in corresponding relation to each given medication requisition.

The medication requisition database 90 may be located in a single location that is either remote from or local to one or more of the patient care provider site or remote fulfillment sites. The medication requisition database 90 may also be provided at a separate location distinct from either the patient care provider site or remote fulfillment site. Further, the medication requisition database 90 may comprise a number of portions or instances that may each be located at separate locations corresponding to or separate from the patient care provider site or remote fulfillment sites.

For example, the medication requisition database 90 may store medication requisition metadata related to the medication requisition. Furthermore, the medication requisition database 90 may store the medication requisition fulfillment cost data and the medication requisition fulfillment timing data employed by the requisition fulfillment logic 30 to produce the decision data for use in selecting one of the plurality of fulfillment sites to fulfill the medication requisition. In this regard, the remote fulfillment sites 60a and 60b may be in operative communication with the medication requisition database 90 to provide medication requisition fulfillment cost data and medication requisition fulfillment timing data corresponding to each respective fulfillment site to the medication requisition database 90.

The medication requisition database 90 may be located remotely from the remote fulfillment sites 60a and 60b as well as the patient care provider 10. Alternatively, the medication requisition database 90 may be located at one of the remote fulfillment sites 60a or 60b or at the patient care provider 10. In any regard, access to the medication requisition database 90 may be facilitated via the medication requisition management network 80.

As may be appreciated, the patient care provider 10 may include an entity authorized by a governing regulatory body (e.g., a pharmacy board) to dispense and prepare medication units for administration to patients. In this regard, the patient care provider may include an authorized entity capable of compounding or otherwise preparing contained medication units for administration to patients. Primarily, examples of patient care providers include the following:

an acute care site;
a hospital;
a home infusion pharmacy;
a physician office;
a free standing infusion clinic; or,
other appropriate healthcare entity authorized to prepare medications.

In an application, the patient care provider may be a hospital having an affiliated pharmacy. It may be appreciated that the affiliated pharmacy may be located onsite with respect to the hospital or the hospital may be affiliated with an offsite pharmacy. In either regard, the medication unit associated with the medication requisition may be administered to the patient at the patient care provider site by the patient care provider. In the case of an offsite pharmacy, the offsite pharmacy may service a plurality of different affiliated hospital sites.

As stated above the medication requisitions generated by the requisition generator 20 may each correspond to a contained unit of a medication for administration to patient. The contained medication unit may be a patient specific unit comprising a medication unit designated for administration to a specific patient. In an embodiment, the contained medication unit may include a non-patient specific unit to be subsequently designated for administration to a specific patient. In an embodiment, a contained medication unit may be a medical source unit (e.g., a compounded or other ingredient) to be used in the preparation of a patient specific unit and/or a non-patient specific unit.

In various embodiments, the contained medication unit may correspond to a variety of different substances that require licensure or other authorization by governing body to prepare. Examples of contained medication units that may correspond to medication requisitions include:
  compounded sterile products;
  injectable medications;
  chemotherapy preparations; or,
  nutritional supplements requiring administration by a patient care provider (e.g., sterile injectable nutritional supplements).
Nutritional supplements may include total parenteral nutrition (TPN) or components of TPN. Furthermore, nutritional supplements may include partial nutritional supplements. The nutritional supplements may include a pre-mix bag, base and additive components separately or in combination, or other forms of nutritional supplements or components thereof. The nutritional supplements may be for administration via intravenous injections, in an edible form, or for use with a feeding tube or the like.

The medication requisition generated by the requisition generator 20 may include data indicative of one or more properties or requirements of the medication requisition. In this regard, the medication requisition may include:
  a medication identity;
  a medication amount;
  a medication concentration;
  information associated with a patient to whom the medication unit associated with the medication requisition is to be administered;
  scheduling information (e.g., an administration time) for the medication unit associated with medication requisition; or
  other appropriate information regarding the medication unit associated with the medication requisition.
In one embodiment, the medication requisition including or associated with any of the foregoing data or other relevant data corresponding to the medication requisition may be stored in the medication requisition database 90.

In any regard, the requisition fulfillment logic 30 may receive the medication requisition and be operable to compare the medication requisition (e.g., medication identity, medication amount, medication concentration, scheduled dispensation time, etc.) in relation to the medication requisition preparation timing data and/or the medication requisition preparation cost data for the plurality of fulfillment sites to determine the decision data for use in determining which fulfillment site may be capable of, or best suited to, fulfill the medication requisition.

In one example, the requisition fulfillment logic 30 may determine which fulfillment site or sites from the plurality of fulfillment sites is capable of fulfilling a medication requisition based on whether a fulfillment site can fulfill the medication requisition prior to the scheduled dispensation time for the medication requisition. In this regard, the medication requisition fulfillment timing data may include, for example:
  medication requisition fulfillment lead time data;
  medication requisition availability data;
  medication requisition delivery schedule data;
  medication requisition efficacy timing data; or
  medication unit component efficacy timing data.
Of those fulfillment sites capable of fulfilling a medication requisition in accord with the scheduled administration time, the medication requisition fulfillment cost data may in turn be used to determine which of the eligible fulfillment sites represent the lowest cost for the fulfillment of the medication requisition. In this regard, the fulfillment site with the lowest cost of fulfillment capable of fulfilling in time for the scheduled administration of the medication unit associated with the medication requisition may be identified as the selected fulfillment site. However, other logic may be applied that may for example, strike different balances between considerations of medication requisition fulfillment cost data, medication requisition fulfillment timing data, or other relevant information for use in producing the decision data. In this regard, the applied logic may be as selectively established by a given patient care provider 10. For example, an algorithm may be established with weighting parameters associated with the relative importance of the medication requisition fulfillment cost data relative to the medication requisition fulfillment timing data. In an example, the patient care provider 10 may predetermine or have control over the weighting of the data. Other factors or data may also be weighted in the algorithm used to arrive at the decision data.

In contemplated implementations, the patient care provider 10 may be able to customize the algorithm and/or factors considered in providing a decision data. For example, the patient care provider may provide overriding conditions that dictate selection of a selected fulfillment site regardless of the decision data. The overriding condition may be based on medication requisitions generated in a specific period, of a specific kind, for administration in a certain period, or other factors related to the medication requisition or fulfillment of the medication requisition.

With further respect to the requisition router 40, as discussed above, the requisition router 40 may be operable to route a medication requisition to a selected one of a plurality of fulfillment sites. As such, the requisition router 40 may be in direct communication with each of the remote fulfillment sites 60*a* and 60*b* as well as the fulfillment site 55 located in the pharmacy 50 of the patient care provider 10. In an embodiment, the routing of medication requisitions from the requisition router 40 to the selected fulfillment site may occur in substantially real-time upon selection of the fulfillment site. In an embodiment, the routing of a medication requisition to the selected fulfillment site may occur periodically as either initiated by the requisition router 40 or the selected fulfillment site. The requisition router 40 may be operable to transmit a group or batch of individual medication requisitions to a single fulfillment site simultaneously in the case where the fulfillment site has been selected as the selected fulfillment site for a number of medication requisitions.

In an embodiment, the requisition router 40 may provide medication requisitions to a fulfillment site by way of the medication requisition management network 80. In this regard, rather than direct communication between the requisition router 40 and remote fulfillment sites 60*a* and 60*b*, the requisition router 40 may communicate with remote fulfillment sites 60a and 60b by way of the medication requisition management network 80.

Each fulfillment site may be operable to provide medication requisition metadata to the medication requisition database 90 (e.g., either directly or via the medication requisition management network 80) regarding medication requisition fulfillment at the fulfillment site.

The medication requisition metadata may include details regarding the composition, preparation, transportation, or other data concerning the medication requisition. The medication requisition metadata may be maintained in corresponding relation to a medication requisition record in the medication requisition database 90. The medication requisition metadata may be periodically updated by a fulfillment site before, during, or after fulfillment of the medication requisition. This may be particularly advantageous in the case of remote fulfillment sites as the patient care provider 10 may access the medication requisition database 90 to obtain information regarding the medication requisition during fulfillment by the remote fulfillment site. However, even in the case of an onsite fulfillment site (e.g., fulfillment site 55), medication requisition metadata may still be provided to the medication requisition database (e.g., to maintain records corresponding to the medication requisition).

The medication requisition metadata may include data corresponding to a plurality of different classes of data relating to the medication requisition including:
  medication source data;
  chain of custody data;
  fulfillment quality data; or
  environmental data.

The medication source data may include data indicative of, for example:
  a manufacturer of a component of the contained medication unit corresponding to the medication requisition,
  a lot number of a component of the contained medication unit corresponding to the medication requisition,
  an expiration date of a component of the contained medication unit corresponding to the medication requisition,
  a serial number of a component of the contained medication unit corresponding to the medication requisition, or
  a drug code indicative of the identity of a component of the contained medication unit corresponding to the medication requisition.

The chain of custody data may include data indicative of, for example:
  a listing of entities in possession of a component of the contained medication unit corresponding to the medication requisition or the contained medication unit corresponding to the medication requisition,
  a listing of users that have taken an action with respect to the contained medication unit corresponding to the medication requisition, wherein the listing of users is correlated to specific actions taken by each user, or
  tracking information corresponding to physical movement of a component of the contained medication unit corresponding to the medication requisition or the contained medication unit corresponding to the medication requisition.

The fulfillment quality data may include data indicative of, for example:
  image data corresponding with a component of the contained medication unit corresponding to the medication requisition or the contained medication unit corresponding to the medication requisition,
  scanned data obtained from a component of the contained medication unit corresponding to the medication requisition,
  analytic data regarding a component of the contained medication unit corresponding to the medication requisition or the contained medication unit corresponding to the medication requisition,
  pharmacist review data corresponding with at least one pharmacist review of a component of the contained medication unit corresponding to the medication requisition or the contained medication unit corresponding to the medication requisition,
  compliance data corresponding with best practices associated with a component of the contained medication unit corresponding to the medication requisition or the contained medication unit corresponding to the medication requisition;
  sterility assessment data corresponding to a component of the contained medication unit corresponding to the medication requisition or the contained medication unit corresponding to the medication requisition,
  a listing of actions corresponding to a component of the contained medication unit corresponding to the medication requisition or the contained medication unit corresponding to the medication requisition,
  time stamp data corresponding to actions corresponding to a component of the contained medication unit corresponding to the medication requisition or the contained medication unit corresponding to the medication requisition, or
  a listing of life cycle events taken with respect a component of the contained medication unit corresponding to the medication requisition or the contained medication unit corresponding to the medication requisition.

The environmental data may be indicative of, for example:
  a temperature to which a component of the contained medication unit corresponding to the medication requisition or the contained medication unit corresponding to the medication requisition has been exposed,
  a temperature to which and corresponding time period for which a component of the contained medication unit corresponding to the medication requisition or the contained medication unit corresponding to the medication requisition has been exposed,
  whether a component of the contained medication unit corresponding to the medication requisition or the contained medication unit corresponding to the medication requisition is refrigerated,
  whether a component of the contained medication unit corresponding to the medication requisition or the contained medication unit corresponding to the medication requisition is frozen,
  a temperature profile experienced by a component of the contained medication unit corresponding to the medication requisition or the contained medication unit corresponding to the medication requisition, or
  accelerometer data corresponding to forces experienced by a component of the contained medication unit corresponding to the medication requisition or the contained medication unit corresponding to the medication requisition.

Accordingly, the fulfillment site that fulfills the medication requisition, be it an onsite fulfillment site 55 or a remote fulfillment site 60a or 60b, may provide medication requisition metadata in connection with the medication requisition.

In addition, in the case of the remote fulfillment site 60a or 60b, the remote fulfillment site may dispatch the medication requisition for physical delivery to patient care provider 10 for administration to the patient 70. Accordingly, the remote fulfillment sites 60a and 60b may be able to ship or otherwise physically dispatch the medication requisition to patient care provider 10. As such, the remote fulfillment site may utilize dedicated delivery vehicles and/or third party delivery services. In either or any regard, the mode of physically dispatching the medication requisition may include tracking data associated with the transport of the medication requisition.

In an embodiment, a remote fulfillment site may collectively send more than one medication requisition to the patient care provider 10. In this regard, a kit may be sent from the remote fulfillment site to the patient care provider 10. The kit may include a plurality of medication requisitions destined to the same patient care provider 10. As such, the kit may include a kit identification. Each medication requisition disposed in the kit may be correlated to the kit identification. In this regard, once the kit is received at the patient care provider, the kit identification may be used to determine that each of the plurality of medication requisitions associated with the kit have likewise been received. Furthermore, any one of the medication requisitions identified that is associated with the kit may indicate that each of the other medication requisitions associated with the kit have been received.

Accordingly, the remote fulfillment site may also provide to the medication requisition management network 80 the kit identification and correlated medication requisitions associated with the kit. In turn, the kit identification and data regarding the correlated medication requisitions associated with the kit may be provided to the patient care provider 10 and/or the medication requisition database 90 for storage.

In an embodiment, each fulfillment site may include a medication requisition management client. The medication requisition management client may be in operable communication with the medication requisition management network 80, wherein the medication requisition management client is operable to receive/send data corresponding with a medication requisition to/from the medication requisition management network 80. In this regard, the medication requisition management client may be employed by the fulfillment site to assist in the preparation of the medication unit associated with a medication requisition in a manner that also generates or documents medication requisition metadata as described above.

Figure 2:
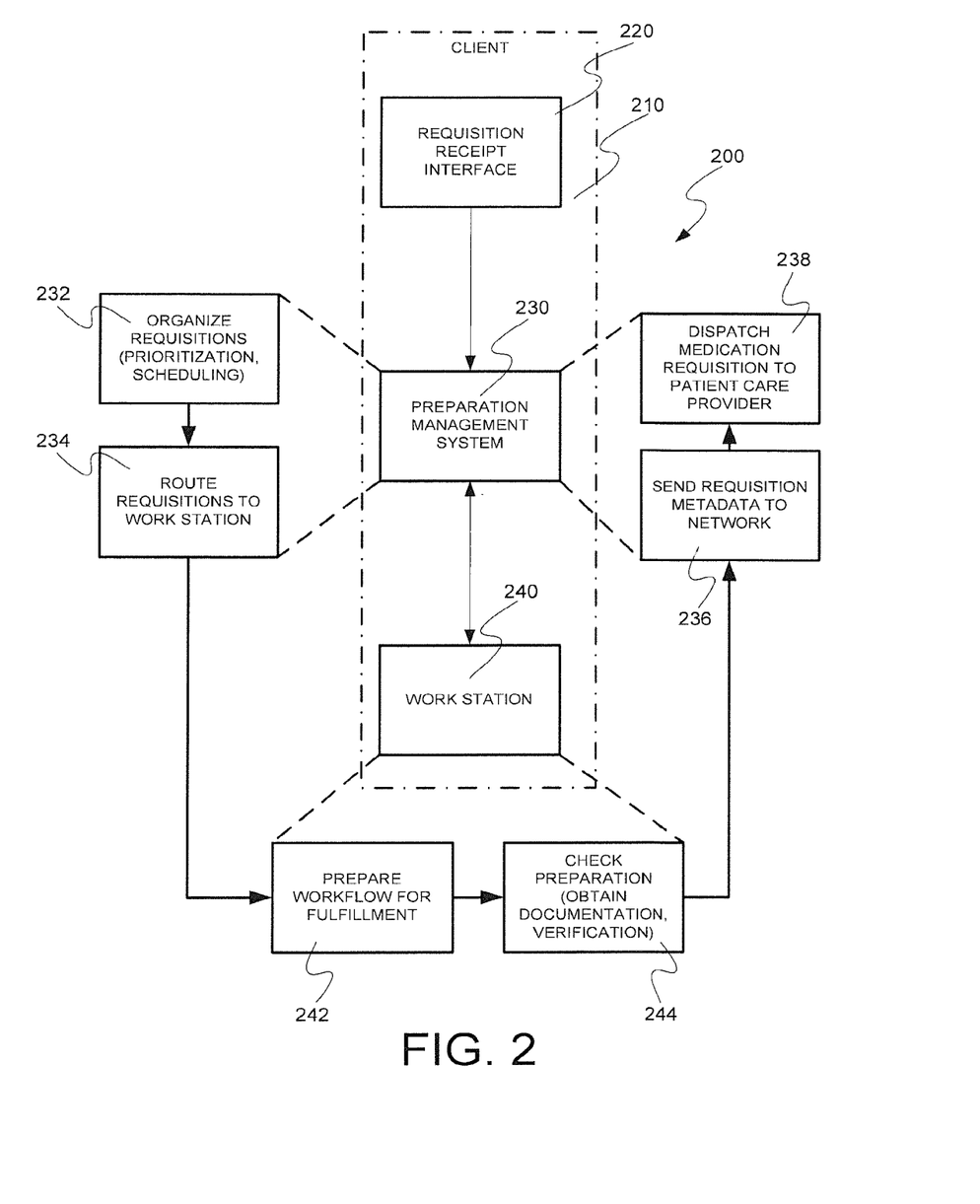
FIG. 2 illustrates an embodiment for use in the system embodiment of FIG. 1.

FIG. 2 illustrates an embodiment of a medication requisition management client 210 that may be used at a fulfillment site 200 to assist in the preparation and/or management of medication requisitions. The client 210 may be a thick or thin client resident at a fulfillment site. For example, the client to 10 may be a thin client such as a web browser executing on a device at the fulfillment site with access to a web-based service. In this regard, a requisition receipt interface 220 may be provided to receive medication requisitions. In furtherance to the above, the requisition receipt interface 220 may communicate directly with a requisition router 40 or may be in operative communication with the requisition router 40 by way of the medication requisition management network 80.

The medication requisitions may be passed on to a requisition preparation management system 230. The requisition preparation management system 230 may be operable to organize 232 medication requisitions received at the medication requisition preparation management client 210. The organization may include prioritization, scheduling, or other tasks associated with the organization or management of medication requisitions. The medication requisition preparation management client 230 may also be operative to route 234 medication requisitions to an appropriate work station 240. In this regard, a plurality of work stations 240 may be provided that may each be suited for different tasks or work flows. As such, depending on the nature of a medication requisition, a particular type of work station 240 may be used to prepare the requisition.

In this regard, the medication requisition preparation management system 230 may be in operative communication with one or more work stations 240. The routing 234 of medication requisitions may be at least partially based on the nature or type of the medication unit and the capabilities of the various work stations 240. In an embodiment, other parameters such as technician schedules, work station schedules, work station location, or other information may be used alone or in combination to route 234 medication requisitions to a particular work station 240.

At the work station 240, a work flow may be prepared 242 that may be used for the preparation of the medication requisition. In this regard, a work flow that is specific to the medication requisition currently being prepared at the work station 240 may be generated and presented to a user at the work station 240. Accordingly, the user may follow a sequence of steps to prepare the medication unit corresponding to the medication requisition based on the prepared work flow presented.

During and/or after the preparation of the medication requisition, the work station 240 may be used to assist in checking 244 the preparation of the medical order. For example, the work station 240 may allow for recording of documentation regarding the preparation of the medication unit such as, for example, barcode scans of products, images of apparatus during or after use in the preparation of the medication unit, or other information related to the preparation of the medication unit. This data may correspond to at least a portion of the medication requisition metadata described above.

Such information collected for the checking 244 may be stored for viewing by appropriate personnel (e.g., a pharmacist) so that the pharmacist may verify the prepared medication requisition prior to the medication requisition leaving the fulfillment site 200. In an embodiment, the information and/or data collected at the work station 240 may be made available to a pharmacist via a network (e.g., the medication requisition management network 80). In this regard, it may be also appreciated that alternate or additional pharmacists (e.g., a pharmacist at the patient care provider 10) may provide concurrent or additional reviews of the medication unit associated with a medication requisition being fulfilled. In any regard, the pharmacist tasked with verifying a medication requisition may access the information and/or data remotely (e.g., in a location in the fulfillment site but outside the room where the medication unit has been prepared or even entirely removed from the fulfillment site premises) via the network 80.

Once the medication requisition has been prepared in accordance with the prepared 242 work flow and checked 242 at workstation 240, the medication requisition preparation management system 230 may send medication requisition metadata to the medication requisition management network 80 for storage in the medication requisition database 90 and/or permission to patient care provider 10. In turn, the medication requisition preparation management system 230 may manage dispatching 238 the medication requisition to the patient care provider 10. In this regard, the medication requisition preparation management system 230 may oversee physical shipment of the medication requisition to the patient care provider 10 in addition to providing data regarding the dedication requisition to the medication requisition management network 80.

Patient care providers currently have limited access to sources of medication units needed for patient care. This limitation derives primarily from the current limitations of their systems and processes to enable only static choices for each specific type of medication unit. These static choices are often determined through completely manual procurement/evaluation processes, and are only revisited episodically. This often results in higher than optimal costs for meeting the provider's needs for medication units, and seriously limits the ability of the patient care provider to efficiently and rapidly respond to events—such as drug shortages or local events that generate significant supply/demand changes—that require a different sourcing approach.

Upon implementation of the present invention, patient care providers will be able to define a set of dynamically-applied rules for selecting sources of each specific type of medication units. This dynamic response capability will enable needs for medication units to be more reliably met on a timely basis, more efficient and effective response for local events and supply issues, and lower cost of medication units taking into consideration new sources of supply.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A pharmacy medication management system, comprising:
   a pharmacy work station that includes a processor that executes machine-readable instructions stored in a memory to configure the pharmacy work station to:
   generate a medication requisition for a contained medication unit based on an order of the contained medication unit,
   execute requisition fulfillment logic to evaluate decision data and identify a selected remote fulfillment site from a plurality of remote fulfillment sites, wherein the decision data is based at least in part on cost data or timing data received at the pharmacy work station from each of the plurality of remote fulfillment sites, and
   execute a requisition router that communicates the medication requisition to the selected remote fulfillment site, wherein the selected remote fulfillment site comprises a work station to prepare and present a work flow that is specific to the medication requisition currently being prepared at the work station including a sequence of steps to prepare the contained medication unit corresponding to the medication requisition based on the work flow, wherein the work station records, utilizing data collection tools, medication requisition metadata comprising bar code scans of products and images of apparatus during or after use in the preparation of the contained medication unit documenting preparation of the contained medication unit in accordance with the work flow, and wherein the selected remote fulfillment site is configured to record medication requisition metadata related to preparation of the contained medication unit in accordance with the work flow; and
   a medication requisition database in operative communication with the pharmacy work station that receives and stores the medication requisition metadata regarding fulfillment of the medication requisition at the selected remote fulfillment site,
   wherein the pharmacy work station associates the medication requisition metadata stored in the medication requisition database with the contained medication unit.

2. The pharmacy medication management system of claim 1, wherein the pharmacy work station is located at a pharmacy of a patient care provider.

3. The pharmacy medication management system of claim 2, wherein the patient care provider comprises an entity authorized by a governing regulatory body to prepare medication requisitions.

4. The pharmacy medication management system of claim 2, wherein the patient care provider comprises one or more of the following:
   an acute care site;
   a hospital;
   a home infusion pharmacy;
   a physician office; or
   a free standing infusion clinic.

5. The pharmacy medication management system of claim 2, wherein the contained medication unit comprises a nutritional supplement or a component of a nutritional supplement that requires administration by the patient care provider.

6. The pharmacy medication management system of claim 2, wherein the contained medication unit is to be administered to a patient at the patient care provider.

7. The pharmacy medication management system of claim 1, wherein the medication requisition database stores the medication requisition metadata in corresponding relation to the medication requisition.

8. The pharmacy medication management system of claim 1, wherein the contained medication unit comprises at least one of the following:
   a patient specific unit comprising a medication unit designated for administration to a specific patient;
   a non-patient specific unit comprising a medication unit to be subsequently designated for administration to a specific patient; or,
   a medication component source unit to be used in the preparation of the patient specific unit or the non-patient specific unit at a pharmacy.

9. The pharmacy medication management system of claim 1, wherein the contained medication unit is received at the pharmacy work station in a kit comprising a plurality of contained medication units, wherein the plurality of contained medication units each have corresponding medication requisitions that are each associable with a kit identifier corresponding with the kit, and wherein said kit identifier comprises a machine readable marking on a container used for handling the plurality of contained medication units at the pharmacy work station.

10. The pharmacy medication management system of claim 1, wherein the cost data and the timing data are stored in the medication requisition database.

11. The pharmacy medication management system of claim 1, wherein the timing data comprises at least one of:
   medication requisition fulfillment lead time data;
   medication requisition availability data;
   medication requisition delivery schedule data;
   medication requisition efficacy timing data; or
   medication unit component efficacy timing data.

12. The pharmacy medication management system of claim 1, wherein the requisition fulfillment logic is at least in part customizable by a user of the pharmacy work station.

13. The pharmacy medication management system of claim 1, wherein the requisition fulfillment logic processes the medication requisition in relation to both the cost data and the timing data.

14. The pharmacy medication management system of claim 13, wherein the requisition fulfillment logic comprises selectable weighting parameters associated with each of the cost data and the timing data.

15. The pharmacy medication management system of claim 14, wherein the weighting parameters associated with the cost data and the timing data are customizable by a user of the pharmacy work station.

16. The pharmacy medication management system of claim 1, wherein the requisition fulfillment logic is operable to automatically select the selected remote fulfillment site at least partially based on the decision data.

17. The pharmacy medication management system of claim 1, wherein the requisition router is operable to automatically route the medication requisition to the selected remote fulfillment site.

18. The pharmacy medication management system of claim 1, wherein the pharmacy work station receives a requisition rejection from the selected remote fulfillment site and the requisition fulfillment logic reprocesses the medication requisition to regenerate another decision data for use in the selection of another one of the plurality of remote fulfillment sites.

19. The pharmacy medication management system of claim 1, wherein the medication requisition database receives and stores metadata regarding fulfillment of additional medication requisitions at other remote fulfillment sites from the plurality of remote fulfillment sites.

20. The pharmacy medication management system of claim 1, wherein the medication requisition metadata comprises at least one of the following types of data:
   medication source data indicative of at least one of:
      a manufacturer of a component of the contained medication unit corresponding to the medication requisition,
      a lot number of a component of the contained medication unit corresponding to the medication requisition,
      an expiration date of a component of the contained medication unit corresponding to the medication requisition,
      a serial number of a component of the contained medication unit corresponding to the medication requisition, or
      a drug code indicative of the identity of a component of the contained medication unit corresponding to the medication requisition;
   chain of custody data indicative of at least one of:
      a listing of entities in possession of a component of the contained medication unit corresponding to the medication requisition or the contained medication unit corresponding to the medication requisition,
      a listing of users that have taken an action with respect to the contained medication unit corresponding to the medication requisition, wherein the listing of users is correlated to specific actions taken by each user, or
      tracking information corresponding to physical movement of a component of the contained medication unit corresponding to the medication requisition or the contained medication unit corresponding to the medication requisition;
   fulfillment data indicative of at least one of:
   image data corresponding with a component of the contained medication unit corresponding to the medication requisition or the contained medication unit corresponding to the medication requisition,
   scanned data obtained from a component of the contained medication unit corresponding to the medication requisition,
   analytic data regarding a component of the contained medication unit corresponding to the medication requisition or the contained medication unit corresponding to the medication requisition,
   pharmacist review data corresponding with at least one pharmacist review of a component of the contained medication unit corresponding to the medication requisition or the contained medication unit corresponding to the medication requisition,
   compliance data corresponding with best practices associated with a component of the contained medication unit corresponding to the medication requisition or the contained medication unit corresponding to the medication requisition,
   sterility assessment data corresponding to a component of the contained medication unit corresponding to the medication requisition or the contained medication unit corresponding to the medication requisition,
   a listing of actions corresponding to a component of the contained medication unit corresponding to the medication requisition or the contained medication unit corresponding to the medication requisition,
   time stamp data corresponding to actions corresponding to a component of the contained medication unit corresponding to the medication requisition or the contained medication unit corresponding to the medication requisition, or
   a listing of life cycle events taken with respect to a component of the contained medication unit corresponding to the medication requisition or the contained medication unit corresponding to the medication requisition; or
   environmental data indicative of at least one of:
   a temperature to which a component of the contained medication unit corresponding to the medication requisition or the contained medication unit corresponding to the medication requisition has been exposed,
   a temperature to which, and corresponding time period for which, a component of the contained medication unit corresponding to the medication requisition or the contained medication unit corresponding to the medication requisition has been exposed,
   whether a component of the contained medication unit corresponding to the medication requisition or the contained medication unit corresponding to the medication requisition is refrigerated,
   whether a component of the contained medication unit corresponding to the medication requisition or the contained medication unit corresponding to the medication requisition is frozen, a temperature profile experienced by a component of the contained medication unit corresponding to the medication requisition or the contained medication unit corresponding to the medication requisition, or accelerometer data corresponding to forces experienced by a component of the contained medication unit corresponding to the medication requisition or the contained medication unit corresponding to the medication requisition.

\* \* \* \* \*